(12) United States Patent
Shroff et al.

(10) Patent No.: US 10,342,230 B2
(45) Date of Patent: Jul. 9, 2019

(54) ZC COMPOSITION COMPRISING MICROENCAPSULATED PENDIMETHALIN

(71) Applicant: UPL LIMITED, Mumbai (IN)

(72) Inventors: Jaidev Rajnikant Shroff, Dubai (AE); Paresh Vithaldas Talati, Mumbai (IN); Rajan Ramakant Shirsat, Mumbai (IN)

(73) Assignee: UPL LIMITED, Mumbai (IN)

( * ) Notice: Subject to any disclaimer, the term of this patent is extended or adjusted under 35 U.S.C. 154(b) by 151 days.

(21) Appl. No.: 15/057,745

(22) Filed: Mar. 1, 2016

(65) Prior Publication Data

US 2016/0174551 A1 Jun. 23, 2016

Related U.S. Application Data

(63) Continuation-in-part of application No. 13/576,181, filed as application No. PCT/IB2011/000144 on Jan. 31, 2011, now Pat. No. 9,288,979.

(30) Foreign Application Priority Data

Feb. 3, 2010 (IN) .......................... 284/MUM/2010

(51) Int. Cl.
*A01N 25/04* (2006.01)
*A01N 33/18* (2006.01)

(52) U.S. Cl.
CPC ............. *A01N 33/18* (2013.01); *A01N 25/04* (2013.01)

(58) Field of Classification Search
CPC ................................ A01N 25/04; A01N 33/18
See application file for complete search history.

(56) References Cited

U.S. PATENT DOCUMENTS

| 5,273,953 | A | * | 12/1993 | Szekely | ................. | A61K 47/14 424/405 |
| 2010/0056373 | A1 | * | 3/2010 | Casana | .................. | A01N 25/14 504/127 |
| 2014/0200141 | A1 | * | 7/2014 | Shroff | .................... | A01N 25/04 504/138 |

FOREIGN PATENT DOCUMENTS

EP 1840145 A1 * 10/2007 ............. A01N 25/28

* cited by examiner

*Primary Examiner* — Johann R Richter
*Assistant Examiner* — Danielle Sullivan
(74) *Attorney, Agent, or Firm* — Seyfarth Shaw LLP

(57) ABSTRACT

The present invention relates to herbicidal compositions for controlling undesirable plant species. A herbicidally effective amount of a ZC formulation comprising microencapsulated pendimethalin and a co-herbicide present in the form of a suspension concentrate is disclosed. The present invention also relates to methods for controlling undesirable plant species comprising applying the herbicidal compositions to the foliage of the plants or to the soil or water containing seeds or other propagating organs thereof.

15 Claims, No Drawings

ZC COMPOSITION COMPRISING MICROENCAPSULATED PENDIMETHALIN

CROSS REFERENCE TO RELATED APPLICATIONS

This application is a continuation-in-part of application Ser. No. 13/576,181, filed Jul. 31, 2012, now U.S. Pat. No. 9,288,979, issued on Mar. 22, 2016, which is the National Stage of International Application No. PCT/IB2011/000144, filed Jan. 31, 2011, which claims the benefit of the Indian Application No. 284/MUM/2010, filed on Feb. 3, 2010, the disclosures of all of which are hereby incorporated by reference in their entirety.

FIELD OF THE INVENTION

The present invention relates to herbicidal compositions. More particularly, the present invention relates to ZC formulations comprising pendimethalin.

BACKGROUND AND PRIOR ART

The type of herbicidal formulation plays an important role in the efficacy of weed control. Various types of herbicidal formulations aim to boost efficacy of the herbicide such that the active ingredient is delivered to the weed with maximum efficacy, minimum waste and prolonged residual effect.

A combination of two active ingredients sometimes leads to incompatibility. It is not uncommon for physical and biological incompatibility to occur, for example insufficient stability of a joint formulation, decomposition of an active ingredient or antagonism of the active ingredients. Incompatibility can lead to the mixture forming a precipitate, or a gel or flakes that settle down rendering the herbicidal mixture and the container useless. This will also result in inefficient spraying of the pesticide, resulting in poor efficacy. It is therefore important for formulators to prepare stable formulations that allow for two incompatible actives to be combined in a single formulation, giving a favourable active profile, high stability and in some cases enhanced synergy, thus permitting reduced rate of application as compared with the individual application of the active compounds. There is therefore a need in the art for a formulation which is stable especially when two incompatible active compounds are combined providing a broader spectrum of control while reducing rate of application.

Herbicidal combinations are used for effective and economical weed control. These combinations offer advantages like broad spectrum of herbicidal action, synergistic effect, prevention of degradation of one herbicide due to the presence of the second herbicide and reduction of dosages of the herbicides.

These herbicidal combinations may be prepared by tank mixing the individual herbicides at the desired rates just before application. However, regulating the rates of individual herbicides in the tank-mixed combinations is a problem for many farmers, who often tend to overdose the herbicides leading to undesired effects in the field crops. Therefore, it is more preferable to prepare formulations comprising the herbicidal combinations at the time of manufacturing. These formulations and their preparation suffer from the complication of mutual degradation and incompatibility of the herbicides when presented and stored in the same formulation for an extended period of time. It is often a challenge for a skilled formulator to prepare a stable composition comprising a combination of two or more active ingredients.

ZC formulations are a combination of capsule suspension and suspension concentrate such that the formulation contains a stable aqueous suspension of microcapsules and solid fine particles (in an aqueous phase), each of which contains at least one active ingredient.

Pendimethalin is a dinitroaniline herbicide. It is a selective herbicide which controls certain broadleaf weeds and grassy weed species in crop and non-crop areas. It is applied to soil at pre-plant, pre-emergence, and post-emergence stages with ground and aerial equipment. It is a low melting active with negligible vapour pressure that is notorious for its problem of staining plants as well as the every other commodity it comes in contact with.

The application PCT/IB2011/002280 discloses a capsule suspension comprising microcapsules in an organic phase and an aqueous phase optionally comprising a second herbicide. The microcapsules encapsulate pendimethalin. The aqueous phase includes an alkali or alkaline earth metal salt of an organic acid.

This application describes that the second herbicide may be either co-microencapsulated with pendimethalin or may be unencapsulated or may be microencapsulated separately and admixed with microencapsulated pendimethalin. The second herbicide is predominantly clomazone or a volatile herbicide such as 2,4-D esters, MCPA esters, triclopyr or picloram. This application does not envisage any further combination partner for encapsulated pendimethalin.

Pendimethalin is known to be incompatible with several classes of herbicides due to its physical characteristics that lead to unstable formulations. The other known water based formulations are also not known to work well for pendimethalin. There is therefore a need in the art for stable, compatible water based formulations of pendimethalin that—
  a. Deliver stain free pendimethalin formulations with a co-active herbicide.
  b. Provide a physically stable formulation of pendimethalin with a co-active herbicide.
  c. Provide a formulation of pendimethalin with a co-active that has prolonged herbicidal effect.
  d. Provide water based environmentally friendly formulation of pendimethalin with a co-active herbicide.
  e. Provide a formulation of pendimethalin that overcomes the incompatibility with other active ingredients.

The present invention therefore aims to solve the problem of incompatibility and stability with the use of ZC formulations, specifically for actives such as pendimethalin when combined with herbicides which are otherwise known to be incompatible with pendimethalin.

Embodiment of the present invention can ameliorate one or more of the above mentioned problems:

SUMMARY OF THE INVENTION

A suspension comprising
  particles of a first herbicide selected from the group consisting of sulfonylurea herbicides, triazinone herbicides, imidazolinone herbicides, triazine herbicides, anilide herbicides, sulphonamide herbicides, organophosphorus herbicides, amide herbicides or alkanamide herbicides
  combined with a suspension of microcapsules of pendimethalin in an aqueous phase, said microcapsules comprising herbicidally effective amount of pendimethalin encapsulated within a polyurea polymeric wall, said polyurea polymeric wall constituting from about 1% to about 20% by total weight of the suspension, said aqueous phase comprising at least one alkali or alkaline earth metal salt of an organic acid selected from the group consisting of acetic acid, propionic acid, citric acid, fumaric acid, tartaric acid, oxalic acid, succinic acid, valeric acid, malonic acid, glutaric acid, adipic acid and phthalic acid, wherein said at least one alkali or alkaline earth metal salt of an organic acid is present in an amount ranging from about 2% to about 55% by weight of the suspension; and wherein said first herbicide displays improved physico-chemical stability in the presence of said encapsulated pendimethalin.

DETAILED DESCRIPTION OF THE INVENTION

It has now been found that encapsulated pendimethalin physico-chemically stabilizes a suspension concentrate of the first herbicide contemplated according to the present invention, which are otherwise known to be incompatible with pendimethalin.

Therefore, in an aspect, the present invention provides a ZC composition comprising:
(a) microencapsulated pendimethalin; and
(b) suspension concentrate of a co-herbicide.

Thus, in an aspect, the present invention provides a suspension comprising
particles of a first herbicide selected from the group consisting of sulfonylurea herbicides, triazinone herbicides, imidazolinone herbicides, triazine herbicides, anilide herbicides, sulphonamide herbicides, organophosphorus herbicides, amide herbicides or alkanamide herbicides
combined with a suspension of microcapsules of pendimethalin in an aqueous phase, said microcapsules comprising herbicidally effective amount of pendimethalin encapsulated within a polyurea polymeric wall, said polyurea polymeric wall constituting from about 1% to about 20% by total weight of the suspension, said aqueous phase comprising at least one alkali or alkaline earth metal salt of an organic acid selected from the group consisting of acetic acid, propionic acid, citric acid, fumaric acid, tartaric acid, oxalic acid, succinic acid, valerie acid, malonic acid, glutaric acid, adipic acid and phthalic acid, wherein said at least one alkali or alkaline earth metal salt of an organic acid is present in an amount ranging from about 2% to about 55% by weight of the suspension; and
wherein said first herbicide displays improved physico-chemical stability in the presence of said encapsulated pendimethalin.

In an embodiment, the preferred suspension is a ZC formulation.

Therefore, embodiments of the present invention can provide a composition comprising ZC formulations comprising encapsulated pendimethalin and at least a co-herbicide.

The present inventors have surprisingly found that, pendimethalin, when combined with actives which are incompatible with pendimethalin when formulated as conventional formulations such as EC, WDG etc., can be combined to form stable formulations when combined in a ZC formulation. Therefore, it was found that combining a suspension concentrate of these herbicides with encapsulated pendimethalin physico-chemically stabilized the resultant ZC formulation, a result which had hitherto not been achieved satisfactorily for these herbicides.

Pendimethalin has two crystallomorphic forms, triclinic pendimethalin I (P1⁻) an orange-coloured thermodynamically stable form, whereas monoclinic pendimethalin II (P21/c) is a bright-yellow meta-stable form. The latter is normally produced first upon cooling molten pendimethalin, whereas the orange form is formed by a polymorphic phase transition which occurs slowly upon long term storage of the yellow form at temperatures below its melting point. The polymorphic phase transition always leads to the particle size growth. This results in the loss of formulation properties like suspensibility, wet sieve retention etc. and also gives rise to a unique problem with the use of pendimethalin, i.e. staining.

Pendimethalin has been known to suffer incompatibilities when combined with certain active compounds. These formulations face problems of incompatibility of active compound, staining of commodities, crystallomorphic transition, particle size growth, loss of physicochemical properties of the formulation on shelf etc. Tank mixing the formulation also leads to flocculation, and separation of the pesticide leads to the non-efficacy of formulation or crop injury.

For example pendimethalin 456 CS when mixed with Metribuzin 75% DF as tank mix was found to lead to flocculation rendering the mixture useless. This was noticed when the pendimethalin 456 CS formulation used was Prowl $H_2O$, a formulation which includes an inorganic salt prior to encapsulation. The inorganic salt was found to enhance the hardness of water, which led to flocculation in the presence of metribuzin 75% DF.

Thus, in an embodiment, the present invention provides a ZC formulation comprising:
a suspension concentrate comprising particles of a first herbicide selected from the group consisting of sulfonylurea herbicides, triazinone herbicides, imidazolinone herbicides, triazine herbicides, anilide herbicides, sulphonamide herbicides, organophosphorus herbicides, amide herbicides or alkanamide herbicides;
combined with a capsule suspension comprising microcapsules of pendimethalin in an aqueous phase, said microcapsules comprising herbicidally effective amount of pendimethalin encapsulated within a polyurea polymeric wall, said polyurea polymeric wall constituting from about 1% to about 20% by total weight of the suspension, said aqueous phase comprising at least one alkali or alkaline earth metal salt of an organic acid selected from the group consisting of acetic acid, propionic acid, citric acid, fumaric acid, tartaric acid, oxalic acid, succinic acid, valerie acid, malonic acid, glutaric acid, adipic acid and phthalic acid, wherein said at least one alkali or alkaline earth metal salt of an organic acid is present in an amount ranging from about 2% to about 55% by weight of the capsule suspension; and
wherein said first herbicide displays improved physico-chemical stability in the presence of said encapsulated pendimethalin.

The ZC formulation comprising encapsulated pendimethalin with a first herbicide greatly improved the stability of the first herbicide which was otherwise susceptible to the degradation in environment of the other herbicides in the formulated product. It is believed that the pendimethalin capsule suspension component used in formulation contains a salted system which provides suitable environment for susceptible actives. The non-staining stable capsule suspension improved the shelf life of pendimethalin as well as decreased staining to a greater degree as compared to commercially available formulations of pendimethalin.

The first herbicides of the present invention are those that are known to be susceptible to degradation or known to be incompatible with pendimethalin, but show remarkable efficacy when stabilised in the ZC formulation of the present invention.

Many sulfonylurea herbicides are known to be incompatible with other active compounds. The known WP formulations of sulfonylurea herbicides such as pyrazosulfuron-ethyl with pendimethalin have been known to be susceptible to degradation and loss of physicochemical properties, whereas the ZC formulation provides excellent stability of active as will be demonstrated in the examples below. The ZC product is stable and retains the physicochemical properties in heat stability test, freeze/thaw test, and in real time storage.

Heat stability studies indicate stability of a product at higher temperature and also give an idea about the shelf life of the product. The freeze/thaw stability indicates the product can withstand low and room temperature cycles. The real time storage at ambient temperature gives shelf life of product.

Thus, in an embodiment, the first herbicide can be selected from but not limited to classes of herbicides selected from sulfonylurea herbicides, triazinone herbicides, imidazolinone herbicides, triazine herbicides, anilide herbicides, quinolinecarboxylic acid herbicides, quinolinecarboxylic acid herbicides, benzoylcyclohexanedione herbicides, sulphonamide herbicides, benzofuranyl alkylsulfonate herbicides, organophosphorus herbicides, chloroacetanilide herbicides, nitrophenyl ether herbicides, sulphonamide herbicides, amide herbicides or alkanamide herbicides and mixtures thereof.

In an embodiment, the sulfonylurea herbicide can be selected from but not limited to amidosulfuron, azimsulfuron, bensulfuron or bensulfuron methyl, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, methiopyrisulfuron, monosulfuron, nicosulfuron, orthosulfamuron, oxasulfuron, primisulfuron, propyrisulfuron, pyrazosulfuron or pyrazosulfuron ethyl, rimsulfuron, sulfometuron, sulfosulfuron, trifloxysulfuron, chlorsulfuron, cinosulfuron, ethametsulfuron, iodosulfuron, iofensulfuron, metsulfuron or metsulfuron methyl, prosulfuron, thifensulfuron, triasulfuron, tribenuron, triflusulfuron, tritosulfuron.

In another embodiment, the sulfonylurea herbicide is pyrazosulfuron or an agrochemically acceptable derivative thereof such as pyrazosulfuron-ethyl.

In an embodiment, the triazinone herbicide can be selected from but not limited to ametridione, amibuzin, ethiozin, hexazinone, isomethiozin, metamitron, metribuzin or trifludimoxazin.

In another embodiment, the triazinone herbicide is metribuzin.

In an embodiment, the imidazolinone herbicide can be selected from but not limited to imazamethabenz, imazamox, imazapic, imazapyr, imazaquin, imazethapyr.

In another embodiment, the imidazolione herbicide is imazapic. In yet another embodiment, the imidazolinone herbicide is imazapic acid.

In an embodiment, the triazine herbicide can be selected from but not limited to dipropetryn, trihydroxytriazine, atrazine, chlorazine, cyanazine, cyprazine, eglinazine, ipazine, mesoprazine, procyazine, proglinazine, propazine, sebuthylazine, simazine, terbuthylazine trietazine, indaziflam, triaziflam, atraton, methometon, prometon, secbumeton, simeton, terbumeton, ametryn, aziprotryne, cyanatryn, desmetryn, dimethametryn, methoprotryne, prometryn, simetryn, terbutryn.

In an embodiment, the triazine herbicide is atrazine.

In an embodiment, the amide herbicide can be selected from but not limited to allidochlor, amicarbazone, beflubutamid, benzadox, benzipram, bromobutide, cafenstrole, CDEA, cyprazole, dimethenamid, dimethenamid-P, diphenamid, epronaz, etnipromid, fentrazamide, flucarbazone, flupoxam, fomesafen, halosafen, huangcaoling, isocarbamid, isoxaben, napropamide, napropamide-M, pethoxamid, propyzamide, quinonamid, tebutam, tiafenacil.

In an embodiment, the amide herbicide is preferably an alkanamide herbicide selected from Napropamide or Napropamide-M.

In an embodiment, the anilide herbicide can be selected from but not limited to chloranocryl, cisanilide, clomeprop, cypromid, diflufenican, erlujixiancaoan, etobenzanid, fenasulam, flufenacet, flufenican, ipfencarbazone, mefenacet, mefluidide, me tamifop, monalide, naproanilide, pentanochlor, picolinafen, propanil, sulfentrazone, triafamone.

In an embodiment, the anilide herbicide is diflufenican or flufenacet.

In an embodiment, the chloroacetanilide herbicide can be selected from but not limited to acetochlor, alachlor, butachlor, butenachlor, delachlor, diethatyl, dimethachlor, ethachlor, ethaprochlor, metazachlor, metolachlor, S-metolachlor, pretilachlor, propachlor, propisochlor, prynachlor, terbuchlor, thenylchlor, xylachlor.

In an embodiment, the chloroacetanilide herbicide is metolachlor or S-metolachlor.

In an embodiment, the quinolinecarboxylic acid herbicides can be selected from but not limited to quinclorac, quinmerac.

In an embodiment, the benzoylcyclohexanedione herbicides can be selected from but not limited to fenquinotrione, ketospiradox, mesotrione, sulcotrione, tefuryltrione, tembotrione.

In an embodiment, the benzofuranyl alkylsulfonate herbicides can be selected from but not limited to benfuresate, ethofumesate.

In an embodiment, the dinitroaniline herbicide can be selected from but not limited to benfluralin, butralin, chlornidine, dinitramine, dipropalin, ethalfluralin, fluchloralin, isopropalin, methalpropalin, nitralin, oryzalin, prodiamine, profluralin, trifluralin.

In an embodiment, the sulfonamide herbicides can be selected from but not limited to asulam, carbasulam, fenasulam, oryzalin, penoxsulam, pyroxsulam.

In an embodiment, the sulphonamide herbicide is oryzlin.

In an embodiment, the nitrophenyl ether herbicides can be selected from but not limited to acifluorfen and salts thereof, aclonifen, bifenox, chlomethoxyfen, chlornitrofen, etnipromid, fluorodifen, fluoroglycofen, fluoronitrofen, fomesafen, fucaomi, furyloxyfen, halosafen, lactofen, nitrofen, nitrofluorfen, oxyfluorfen.

In an embodiment, the organophosphorus herbicides can be selected from but not limited to amiprofos-methyl, amiprophos, anilofos, bensulide, bilanafos, butamifos, clacyfos, fosamine, glufosinate and all its salts and esters, glufosinate-P, glyphosate and all its salts and esters, huangcaoling, piperophos, shuangjiaancaolin.

In an embodiment, the organophosphorus herbicide is glufosinate or a salt or a derivative thereof, and glyphosate or a salt or a derivative thereof.

Therefore, in a preferred embodiment, the first herbicide is selected from the group consisting of pyrazosulfuron-ethyl, metribuzin, imazapic acid, atrazine, napropamide, napropamide-M, flufenacet, oryzalin, glufosinate, glyphosate and agrochemically acceptable salts and derivatives thereof.

Therefore, in this embodiment, the present invention provides a ZC composition comprising:
(a) microencapsulated pendimethalin; and
(b) suspension concentrate of a co-herbicide selected from the group consisting of pyrazosulfuron-ethyl, metribuzin, imazapic acid, atrazine, napropamide, napropamide-M, flufenacet, oryzalin, glufosinate, glyphosate and agrochemically acceptable salts and derivatives thereof.

In another embodiment, the present invention provides a suspension comprising
particles of a first herbicide selected from the group consisting of pyrazosulfuron-ethyl, metribuzin, imazapic acid, atrazine, napropamide, napropamide-M, flufenacet, oryzalin, glufosinate, glyphosate and agrochemically acceptable salts and derivatives thereof
combined with a suspension of microcapsules of pendimethalin in an aqueous phase, said microcapsules comprising herbicidally effective amount of pendimethalin encapsulated within a polyurea polymeric wall, said polyurea polymeric wall constituting from about 1% to about 20% by total weight of the suspension, said aqueous phase comprising at least one alkali or alkaline earth metal salt of an organic acid selected from the group consisting of acetic acid, propionic acid, citric acid, fumaric acid, tartaric acid, oxalic acid, succinic acid, valerie acid, malonic acid, glutaric acid, adipic acid and phthalic acid, wherein said at least one alkali or alkaline earth metal salt of an organic acid is present in an amount ranging from about 2% to about 55% by weight of the suspension; and
wherein said first herbicide displays improved physico-chemical stability in the presence of said encapsulated pendimethalin.

In another embodiment, the present invention provides a ZC formulation comprising:
a suspension concentrate comprising particles of a first herbicide selected from the group consisting of pyrazosulfuron-ethyl, metribuzin, imazapic acid, atrazine, napropamide, napropamide-M, flufenacet, oryzalin, glufosinate, glyphosate and agrochemically acceptable salts and derivatives thereof
combined with a capsule suspension comprising microcapsules of pendimethalin in an aqueous phase, said microcapsules comprising herbicidally effective amount of pendimethalin encapsulated within a polyurea polymeric wall, said polyurea polymeric wall constituting from about 1% to about 20% by total weight of the suspension, said aqueous phase comprising at least one alkali or alkaline earth metal salt of an organic acid selected from the group consisting of acetic acid, propionic acid, citric acid, fumaric acid, tartaric acid, oxalic acid, succinic acid, valeric acid, malonic acid, glutaric acid, adipic acid and phthalic acid, wherein said at least one alkali or alkaline earth metal salt of an organic acid is present in an amount ranging from about 2% to about 55% by weight of the capsule suspension; and
wherein said first herbicide displays improved physico-chemical stability in the presence of said encapsulated pendimethalin.

In an embodiment, the encapsulated pendimethalin component may comprise another herbicide which is different from the first herbicide. This additional herbicide may be typically co-encapsulated with pendimethalin within the microcapsules. The choice of this additional herbicide is not particularly limiting and may be selected to be any herbicide that is compatible with pendimethalin.

The ZC formulations according to the present invention are prepared such that microencapsulation of pendimethalin is carried out first and the resulting microcapsule dispersion, if appropriate after partial or complete removal of the liquid phase, is mixed with a suspension of the first herbicide.

In the embodiment wherein the first herbicide is a liquid, it is usually absorbed/adsorbed on a particulate solid support. The solid support particles, having the liquid herbicide absorbed/adsorbed therein are thereafter conventionally used to prepare a suspension to be combined with encapsulated pendimethalin.

In an aspect, the capsule suspension of pendimethalin can be prepared by encapsulating pendimethalin within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid.

The suspension concentrate of the present invention can be prepared by blending surfactants, co-formulants, water and the first herbicide.

The capsule suspension comprising pendimethalin may be prepared by a process as described in the above noted parent applications.

The process comprises:
(a) forming an aqueous solution comprising at least one surfactant and a pre-defined amount of at least one alkali or alkaline earth metal salt of an organic acid;
(b) forming an organic phase by melting a herbicidally effective amount of pendimethalin active ingredient and adding a predetermined amount of a first wall forming component to said organic phase;
(c) dispersing said organic phase in said aqueous solution to obtain an emulsion; and
(d) adding a second wall forming component to said emulsion such that said second wall forming component reacts with said first wall forming component comprised within said emulsion to polymeric wall encapsulating at least said herbicidally effective amount of pendimethalin active ingredient.

The suspension concentrate comprising the selected first herbicides according to the present invention may be prepared in the following manner:
(a) forming a slurry comprising water, surfactants and additional coformulants with the first herbicide or mixtures thereof; and
(b) milling the slurry to a desired particle size at ambient temperature.

The microcapsules and the suspension concentrate may then be mixed together to form stable ZC formulation.

In alternate embodiments, the capsule polymeric wall of the present invention may be any known shell wall material but is preferably selected from polyurea, polyurethane, polyamide, polycarbonate, polysulfonamide shell wall or a crosslinked or non-crosslinked combinations thereof. Preferably, the capsule polymeric wall is polyurea wall.

The capsule polymeric wall of the present invention is formed using interfacial polymerization by contacting said first wall forming component with a second wall forming component as is conventionally known in the art.

The first wall forming component is preferably selected from a polyisocyanate, a polyacid chloride, a polychloroformate and a polysulfonyl chloride. The second wall forming component is preferably selected from a polyamine and polyol. Preferably, a polyisocyanate reacts with a polyamine to form a polyurea capsule wall of the present invention.

The preferred polyisocyanates as the first wall forming component may be selected from tetramethylene diisocyanate, pentamethylene diisocyanate, hexamethylene diisocyanate, toluene diisocyanate, diphenylmethene-4,4'-diisocyanate, polymethylene polyphenylene isocyanate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4'4"-triphenylmethane triisocyanate. A preferred polyisocyanate first wall forming component is polymethylene polyphenylisocyanate.

The preferred polyamines as the second wall forming components may be selected from ethylenediamine, propylene-1,3-diamine, tetramethylenediamine, pentamethylenediamine, 1,6-hexamethylenediamine, diethylenetriamine, triethylenetetramine, tetraethylenepentamine, pentaethylenehexamine, 4,9-dioxadodecane-1, 1,2-diamine, 1,3-phenylenediamine, 2,4- and 2,6-toluenediamine and 4,4'-diaminodiphenylmethane or acid addition salt thereof. The preferred polyamine according to the present invention is diethylenetriamine.

The first wall forming component comprises from about 0.1% to about 20% by weight of the organic phase of the present invention. The second wall forming component is preferably present in an amount of about 0.3% to 7.5% by weight relative to the total weight of the formulation.

In a further preferred embodiment, the preferred polyurea polymeric shell wall may be formed by a self-condensation reaction of a polyisocyanate wall forming component. In this embodiment, the process for the preparation of the capsule suspension formulation according to the present invention comprises establishing a physical dispersion of an organic phase in the aqueous phase. In this embodiment, the organic phase comprises the organic isocyanate intermediate such as hereinabove described along with the pendimethalin active ingredient.

In an embodiment the surfactants may be selected from ethylene oxide/propylene oxide condensates; alkyl, aryl- and aryl, arylethoxylates and derivatives thereof; lignosulfonates; cresol- and naphthalene-formaldehyde condensates and sulfonates; polycarboxylates and derivatives thereof; and mixtures thereof.

In an embodiment, the coformulants may be selected from antifoaming agents, antifreezing agents, suspending agents, preservatives and thickening agents.

In an embodiment, the antifoaming agents may be selected from silicone emulsions such as SAG-1572, long-chain alcohols, fatty acids, organofluorine compounds and mixtures thereof.

In an embodiment, the slurry comprising the first herbicide, from which its suspension concentrate is prepared, may be milled to a particle size of $D_{90}$ 8-10 microns.

Thus, in another aspect, the present invention provides a process for the preparation of a ZC formulation, said process comprising:

(a) forming an aqueous solution comprising at least one surfactant and a pre-defined amount of at least one alkali or alkaline earth metal salt of an organic acid;

(b) forming an organic phase by melting a herbicidally effective amount of pendimethalin active ingredient and adding a predetermined amount of polyisocyanate wall forming component;

(c) dispersing said organic phase in said aqueous solution to obtain an emulsion to form an interface between the discrete droplets of organic phase and the aqueous phase; and (d) maintaining said emulsion for a sufficient period of time to allow substantial completion of the self-polymerization reaction of polyisocyanate such that said liquid droplets in the organic phase are converted to capsules comprising polyurea shells enclosing pendimethalin active ingredient;

(e) forming slurry comprising dispersant, water, surfactants and coformulants to obtain slurry and adding the first herbicide herbicide to the slurry;

(f) milling the slurry to a desired particle size and mixing the obtained dispersion with the dispersion of the capsule suspension or mixing drained microcapsules to the suspension; and (g) combining the microencapsulated part of the formulation with the suspension.

In an embodiment, the emulsion of said organic phase in said aqueous solution may be preferably heated to a temperature of between 20° C. to about 100° C., preferably to about 35-85° C. to accelerate the self-condensation of the polyisocyanate pre-polymer.

However, irrespective of whether self-condensation of the first wall forming component is preferred or condensation between a first and a second wall forming component is preferred, the relative quantities of the organic and the aqueous phases are not critical for the process of the present invention. Typically, the organic phase may comprise up to about 75% by volume of the total emulsion and the emulsion comprises discrete droplets of an organic solution dispersed in the aqueous solution.

The droplet size in the emulsion was not found critical to the formulation and process of the present invention but may be found between 0.5 microns to about 4000 microns, which may be further adapted using a high shear device to preferably about 1 micron to about 100 microns. It has further been found that the in situ self-condensation polymerization reaction is self-terminating and is generally allowed to run to completion. The reaction typically runs to completion within the span of a few minutes to a few hours. In a preferred embodiment, the reaction is typically allowed to run for about 2 to 3 hours.

However, the preferred polyurea polymeric shell may be formed by a self-condensation reaction of a preferred polyisocyanate using other preferred methods. In one such preferred embodiment, the formation of the polyurea capsule enclosure around the dispersed organic droplets could be brought about by (a) dispersing the organic phase droplets in the continuous aqueous phase to form an emulsion followed by heating the emulsion resulting therefrom; or (b) heating the continuous aqueous phase and dispersing the organic phase droplets in the heated continuous aqueous phase to form the emulsion thereby effecting the desired self-condensation reaction at the interface between the organic droplets and the aqueous phase.

The alkali or alkaline earth metal salt of an organic acid as used herein is preferably selected from alkali or alkaline earth metal salt of a weak organic acid selected from acetic acid, propionic acid, citric acid, fumaric acid, tartaric acid, oxalic acid, succinic acid, valeric acid, malonic acid, glutaric acid, adipic acid and phthalic acid.

The preferred alkali metal is selected from sodium and potassium. In a more preferred embodiment, the preferred alkali metal is sodium.

In another preferred embodiment, the alkali or alkaline earth metal salt of an organic acid is selected from sodium acetate or disodium succinate.

The aqueous solution comprises at least one surfactant. Preferably, the surfactant may be selected from the group comprising ethoxylated lignosulfonic acid salts, lignosulfonic acid salts, oxidized lignins, lignin salts, salts of styrene-maleic anhydride copolymers, polyvinyl alcohol, salts of partial esters of styrene-maleic anhydride copolymers, partial salts of polyacrylic acid and partial salts of polyacrylic acid terpolymers.

Preferably, the surfactant is lignosulfonate of calcium or sodium.

Preferably, the surfactant is present in an amount of about 0.2% to about 5% by weight of the formulation.

The aqueous solution of the present invention includes an alkali or alkaline earth metal salt of an organic acid or mixtures thereof in an amount of from about 2% to about 55% by weight of the formulation.

The term "herbicidally effective amount" of pendimethalin or the first herbicide (hereinafter the "co-herbicide") is that quantity of pendimethalin or the co-herbicide respectively which when applied in that amount will provide the required control of weeds. The particular amount is dependent upon many factors including, for example, the crop, weeds sought to be controlled and environmental conditions. The selection of the proper quantity of active agent to be applied, however, is within the expertise of one skilled in the art and is not considered particularly limiting.

The microcapsules of the present invention comprise from about 5% to about 60% of pendimethalin. The suspension concentrate of the present invention comprise from 5% to about 60% of the co-herbicide.

In a preferred embodiment, the polymeric shell wall according to the present invention constitutes from about 1% by weight to about 20% by weight of the formulation. In another preferred embodiment, the polymeric shell wall constitutes about 2.5% by total weight of the formulation.

The microcapsules of the present invention preferably have a particle size of about 2 micrometers to 50 micrometers.

In an embodiment, the slurry may be milled to a particle size of $D_{90}$ 8-10 microns Preferably, the formulation of the present invention comprise an anti-foam in an amount of about 0.01% to about 5% by weight of the formulation. Such suitable anti-foams are conventionally known in the art and are not particularly limiting.

Preferably the formulation of the present invention comprise surfactants in the form of lignosulfonate salts, most preferably sodium or calcium salts.

The microcapsules of the present invention may further include a rheology modifier. The preferred rheology modifier includes xanthan gum and clay, which may be present in an amount of about 0.01% to about 3% by weight of the formulation.

The capsule suspension formulation according to the present invention may further be neutralized preferably with an organic acid to regulate the pH within the desired range. Accordingly, the formulations according to the present invention additionally comprises from about 0.1% to about 10% of a neutralizing acid, which may be an organic acid. Preferably, the neutralizing acid is acetic acid.

Another advantage of the addition of a neutralizing acid is that the added acid combines with the unreacted amines to form an ammonium salt, which substantially reduces the amount of external salt addition required for achieving an appreciable non-staining property. The addition of a neutralizing acid is particularly beneficial in reducing the level of inorganic salt of the prior art formulations, which has been reported to aggravate the problem of phytotoxicity in various tested plants. In this embodiment of the present invention, a significantly large quantity of amines in excess may be employed to further reduce the external addition of a salt by in situ generation of a larger amount of salt upon reaction with the neutralizing acid.

In a preferred embodiment, the formulations according to the present invention may additionally comprise a biocide in an amount of from about 0.01% to about 3% by weight of the formulation.

In an aspect, the present invention provides a ZC composition comprising encapsulated pendimethalin and a co-herbicide selected from the group consisting of pyrazosulfuron-ethyl, metribuzin, imazapic acid, atrazine, napropamide, napropamide-M, flufenacet, oryzalin, glufosinate, glyphosate and agrochemically acceptable salts and derivatives thereof, in a suspension concentrate.

In an aspect, the present invention provides a ZC composition comprising encapsulated pendimethalin and a suspension concentrate comprising at least two co-herbicides, at least one of which co-herbicides is selected from the group consisting of pyrazosulfuron-ethyl, metribuzin, imazapic acid, atrazine, napropamide, napropamide-M, flufenacet, oryzalin, glufosinate, glyphosate and agrochemically acceptable salts and derivatives thereof.

In another aspect, the present invention also provides a process for the preparation of a ZC formulation, said process comprising:

(a) forming an aqueous solution comprising at least one surfactant and a pre-defined amount of at least one alkali or alkaline earth metal salt of an organic acid and optionally heating said aqueous solution;

(b) forming an organic phase by melting a herbicidally effective amount of pendimethalin active ingredient and adding a predetermined amount of a first wall component to said organic phase;

(c) dispersing said organic phase in said aqueous solution to obtain an emulsion and optionally heating said formed emulsion;

(d) adding a second wall forming component to said emulsion such that said second wall forming component reacts with said first wall forming component comprised within said emulsion to form polymeric wall encapsulating at least said herbicidally effective amount of pendimethalin active ingredient;

(e) forming a slurry comprising water, at least one co-herbicide, surfactants and co-formulants;

(f) milling the slurry to a desired particle size to form a stable suspension of co-herbicide;

(g) combining the microencapsulated part (d) of the formulation with the suspension.

Preferably, said step of forming an aqueous solution comprises heating water to an elevated temperature, preferably about 60° C. and adding said surfactant and said alkali or alkaline earth salt of an organic acid. In a preferred embodiment, an anti-foam is also added to the aqueous solution.

In another preferred embodiment, said first wall forming component is preferably added to said molten pendimethalin while stirring.

In yet another preferred embodiment, said step of dispersing said organic phase in said aqueous solution to obtain an emulsion is carried out to a desired particle size.

In another preferred embodiment, subsequent to the addition of the second wall forming component to the emulsion, the reaction is allowed to continue for a predetermined time, preferably one hour under stirring, while the reaction mass is maintained at an elevated temperature.

Subsequently, the reaction mixture is neutralized with an organic acid. The neutralization is carried out preferably to attain a formulation pH of from about 6.5 to about 7.5.

Subsequently, xanthan gum is preferably added under stirring.

In a preferred embodiment, a biocide is added to obtain the target formulation.

In a preferred embodiment, the process of the present invention is carried out at an elevated temperature to maintain the pendimethalin active ingredient in a molten state and to enhance the rate of polymeric wall formation. In this embodiment, the process of the present invention is preferably carried out at a temperature of about 35° C. to about 85° C., and is more preferably conducted at a temperature of about 50° C. to 65° C.

Thus, in an embodiment the present invention also provides a process for the preparation of a capsule suspension formulation, said process comprising:
(a) forming an aqueous solution comprising at least one surfactant and a pre-defined amount of at least one alkali or alkaline earth metal salt of an organic acid and optionally heating said aqueous solution;
(b) forming an organic phase by melting a herbicidally effective amount of pendimethalin active ingredient and an additional herbicide and adding a predetermined amount of a first wall component to said organic phase;
(c) dispersing said organic phase in said aqueous solution to obtain an emulsion and optionally heating said formed emulsion; and
(d) adding a second wall forming component to said emulsion such that said second wall forming component reacts with said first wall forming component comprised within said emulsion to polymeric wall encapsulating at least said herbicidally effective amount of pendimethalin and any additional herbicide;
(e) forming a slurry comprising water, a co-herbicide, surfactants and co-formulants;
(f) milling the slurry to a desired particle size to form a stable suspension of co-herbicide;
(g) combining the microencapsulated part (d) of the formulation with the suspension.

In an embodiment, the ZC formulation of the present invention comprises a mixture of the pendimethalin component and the co-herbicide suspension component in a predetermined ratio. In an embodiment, the pendimethalin component and the co-herbicide component are admixed in ratio of from about 1:90 to about 90:1, preferably in a ratio of from about 1:10 to about 10:1.

In another non-limiting embodiment, the pendimethalin component and the co-herbicide component are admixed in a ratio of from about 1:2 to about 1:3.

The invention further relates to a method for controlling weeds at a locus by applying to the locus of the weeds a herbicidally effective amount of a ZC formulation comprising microencapsulated pendimethalin and a co-herbicide.

Preferably, the present invention provides a method for controlling undesirable plant species which comprises applying to the foliage of the plants or to the soil or water containing seeds or other propagating organs thereof, a herbicidally effective amount of a ZC formulation comprising microencapsulated pendimethalin and a co-herbicide present in a suspension concentrate.

Alternatively, the present invention provides a method for controlling undesirable plant species which comprises applying to the foliage of the plants or to the soil or water containing seeds or other propagating organs thereof, a herbicidally effective amount of a ZC formulation comprising pendimethalin, co-microencapsulated with an additional herbicide, and the first herbicide present as suspension concentrate of the said formulation.

In an embodiment, the composition of the present invention can be packaged as a kit-of-parts. In an embodiment a kit-of-parts may contain various components of the formulation of the present invention that may can be mixed as instructed prior to spraying.

Accordingly, one aspect of the present invention can provides a multi-pack herbicidal product for controlling weeds at a locus comprising components of the present invention and a manual. The instruction manual includes instructions for administering the components of the ZC formulation.

In an embodiment, the instruction manual includes instructions for administering the ZC formulation at a locus or to a foliage of the plants or to the soil or to water containing seeds or other plant propagating organs.

In another embodiment, the instruction manual includes instructions for admixing the encapsulated pendimethalin component with the first herbicide suspension concentrate component in a predetermined ratio. In an embodiment, the instruction manual instructs the user to admix the pendimethalin component and the first herbicide component in a ratio of from about 1:10 to about 10:1, preferably in a ratio of from about 1:2 to 1:3.

In an embodiment, the combination kit is packed in a package or a carton. In another embodiment, the instruction manual may be printed on said package or carton or may be printed on a booklet that may be included within the package or the carton.

The herbicidal composition and method of the present invention can offer some particular advantages over the compositions known in the prior art. The novel combination of microencapsulated pendimethalin and the first herbicide in a ZC formulation allow for stable formulations which allow broad spectrum coverage of weeds. The ZC formulations greatly improve stability and allow for combination of incompatible actives. The novel ZC formulation also has the added advantage of being a non-staining pendimethalin composition.

The invention shall now be described with reference to the following specific examples. It should be noted that the example(s) appended below illustrate rather than limit the invention, and that those skilled in the art will be able to design many alternative embodiments without departing from the scope of the present invention.

EXAMPLES

Example 1: Pendimethalin Sulfonylurea ZC Formulation

A) Pendimethalin Capsule Suspension Composition:

| Sr no | Ingredients | % w/w |
| --- | --- | --- |
| 1 | Pendimethalin technical 40 @ 97% purity tech | 40.41 |

-continued

| Sr no | Ingredients | % w/w |
|---|---|---|
| 2 | PMPI | 1.01 |
| 3 | Water | 38.21 |
| 4 | Borresperse Na | 2.50 |
| 5 | Na- acetate (an) | 15.30 |
| 6 | Defoamer | 0.10 |
| 7 | EDA | 0.23 |
| 8 | DETA | 0.26 |
| 9 | Acetic acid | 0.35 |
| 10 | 2% Rhodopol-23 gel | 1.50 |
| 11 | Proxel GXL | 0.13 |
| 12 | Total | 100.00 |

The above composition was prepared by following the present encapsulation process as follows:

An aqueous solution was created by heating water to 60° C. while adding sodium lignosulfonate and subsequently sodium acetate, then antifoam while stirring. A sufficient quantity of water was separately preserved for the amine and gum preparations. Meanwhile, organic phase was formed by melting pendimethalin technical by heating it to 60° C. and then adding polymethylene polyphenylisocyanate (PMPI) while stirring. The aqueous and organic phases were maintained at 60° C. throughout reaction. The organic phase was emulsified in the aqueous solution till the desired particle size. DETA/EDA was added to the resultant emulsion. Reaction was allowed to proceed for 1 hour while maintaining at 60° C. under stirring. The reaction mixture was allowed to cool to ambient temperature for 15 minutes before neutralizing with acetic acid. The formulation was neutralized to pH 8.0 in cold conditions or at a pH of 7 in warmer conditions. The neutralized formulation was filtered through a 60 mesh sieve. A xanthan gum-water slurry was separately prepared and added to the above formulation under stirring for at least 15 minutes. Lastly, a biocide was added and the final product was filtered through a 60-mesh sieve. The particle size was measured using a Horiba LA-910 or CILAS 1064.

Concentrate Slurry of Sulfonyl Urea

| Sr. no | Component of Formulation | Pyrazosulfuron ethyl | Bensulfuron Methyl | Sulfosulfuron |
|---|---|---|---|---|
| 1 | Sulfonylurea 51 @ 98% purity tech | 52.04 | 52.04 | 52.04 |
| 2 | Borresperse NA | 06.00 | 06.00 | 06.00 |
| 3 | Defoamer (SAG-1572) | 00.10 | 00.10 | 00.10 |
| 4 | Water (QS) | 41.86 | 41.86 | 41.86 |
|  | Total | 100.00 | 100.00 | 100.00 |

The above composition was prepared by following the process as follows:

An aqueous solution was prepared using water, sodium lignosulfonate, and antifoam agent. Sulfonylurea herbicide was added to the mixture and homogenized. The homogenized solution was ground to particle size of $D_{90}$ 8-10 microns in a bead mill to form slurry.

The microencapsulated pendimethalin was added to the suspension concentrate of sulfonylurea to form the final ZC formulation. The resulting formulation was subjected to stability tests:

Example 2: Physicochemical Data
Pendimethalin+Sulfonylurea ZC

| Sr. no | Properties | Pyrazosulfuron ethyl | | Bensulfuron Methyl | | Sulfosulfuron | |
|---|---|---|---|---|---|---|---|
| | | Ambient | 14 days AHS at 54° C. | Ambient | 14 days AHS 54° C. | Ambient | 14 days AHS 54° C. |
| 1 | Appearance | Orange yellow capsule suspension | Flowable, Orange yellow capsule suspension | Orange yellow capsule suspension | Flowable, Orange yellow capsule suspension | Orange yellow capsule suspension | Flowable, Orange yellow capsule suspension |
| 2 | Pendimethalin ai content g/L | 458.5 | 457.2 | 452.01 | 450.60 | 459.38 | 457.38 |
| 3 | SU ai content g/L | 11.7 | 11.36 (2.9% degradation) | 27.53 | 26.99 (1.96% degradation) | 33.43 | 32.67 (2.27% degradation) |
| 4 | Suspensibility % w/w | 100.26 | 100.9 | 98.67 | 98.28 | 99.10 | 98.69 |
| 5 | Spontaneity of dispersion % w/w | 100.16 | 100.29 | 99.14 | 98.98 | 99.26 | 99.14 |
| 6 | Wet sieve retention % w/w | 0.02 | 0.02 | 0.05 | 0.12 | 0.03 | 0.09 |
| 7 | pH 1% aqueous | 7.43 | 7.36 | 7.82 | 7.69 | 7.85 | 7.80 |

|  |  | Pyrazosulfuron ethyl | | Bensulfuron Methyl | | Sulfosulfuron | |
|---|---|---|---|---|---|---|---|
| Sr. no | Properties | Ambient | 14 days AHS at 54° C. | Ambient | 14 days AHS 54° C. | Ambient | 14 days AHS 54° C. |
| 8 | Pourability rinse residue % | 0.1 | 0.12 | 0.06 | 0.11 | 0.5 | 0.10 |
| 9 | Particle size. D-50 | 5.58 | 5.57 | 5.36 | 5.57 | 5.29 | 5.50 |
|  | D-4,3 | 6.59 | 6.72 | 6.61 | 6.69 | 6.53 | 6.62 |
|  | D-90 | 13.28 | 13.32 | 14.10 | 14.17 | 13.26 | 13.60 |

Conclusion:

1) All three formulations showed good stability of physicochemical properties, suspensibility, spontaneity of dispersion, pH range, wet sieve retention, particle size in AHS at 54° C.

2) All three formulations showed improved active ingredient stability in AHS.

Example 3: Low Temperature Stability Pendimethalin+PSE ZC

| Sr. no | Properties | | Before freeze/Thaw test | After freeze/Thaw test |
|---|---|---|---|---|
| 1 | Appearance | | Orange yellow capsule suspension | Flowable, Orange yellow capsule suspension |
| 2 | Pendimethalin ai content g/L | | 458.5 | 458.3 |
| 3 | Pyrazosulfuron ethyl ai content g/L | | 11.7 | 11.65 |
| 4 | Pendimethalin free ai % w/w | | 0.13 | 0.16 |
| 5 | Suspensibility % w/w | | 98.3 | 98.56 |
| 6 | Wet sieve retention % w/w | | 0.02 | 0.03 |
| 7 | pH 1% aqueous | | 7.43 | 7.36 |
| 8 | Particle size. | D-50 | 5.58 | 5.59 |
|  |  | D-4.3 | 6.59 | 6.61 |
|  |  | D-90 | 13.28 | 13.40 |

Conclusions:

Free pendimethalin content in the formulation was very low, and both capsule stability and suspension stability in low temperature was excellent.

Example 4: Real Time Stability Data for Pendimethalin+Pyrazosulfuron Ethyl ZC

| Sr no | Properties | | Zero day | 6 month | 12 month |
|---|---|---|---|---|---|
| 1 | Appearance | | Orange yellow capsule suspension | Flowable, Orange yellow capsule suspension | Flowable, Orange yellow capsule suspension |
| 2 | Pendimethalin ai content g/L | | 451.6 | 450.04 | 449.90 |
| 3 | Pyrazosulfuron ethyl ai content g/L | | 11.46 | 11.22 (2.09% degradation) | 11.15 (2.7% degradation) |
| 4 | Suspensibility % w/w | | 99.52 | 99.0 | 98.5 |
| 5 | Spontaneity of dispersion % w/w | | 100.93 | 100.5 | 99.85 |
| 6 | Wet sieve retention % w/w | | 0.04 | 0.04 | 0.04 |
| 7 | pH as such | | 7.33 | 7.30 | 7.45 |
| 9 | Particle size | D-50 | 6.17 | 6.15 | 6.16 |
|  |  | D-4.3 | 9.78 | 9.76 | 9.86 |
|  |  | D-90 | 20.89 | 21.2 | 21.1 |

Conclusion:

Formulation was stable over a period of 12 months. Pyrazosulfuron ethyl and Pendimethalin showed very little degradation.

Example 5: Preparation of Pendimethalin+Triazinone ZC Composition

Pendimethalin capsule suspension was prepared as described in example 1. Metribuzin suspension concentrate was prepared according to the following formulation:

| Sr. no | Component of Formulation | % |
|---|---|---|
| 1 | Metribuzin tech 52 @ 95% purity tech | 54.74 |
| 2 | Borresperse Na | 7.50 |
| 4 | Defoamer | 0.10 |
| 6 | water | 37.66 |
| | Total | 100.00 |

The above composition was prepared by the following process:

An aqueous solution was prepared using water, sodium lignosulfonate, and antifoam agent. Metribuzin was added to the mixture and homogenized. The homogenized solution was ground to particle size of $D_{90}$ 8-10 microns in a bead mill to form slurry.

The microencapsulated pendimethalin was added to the suspension concentrate of metribuzinto form the final ZC formulation. The resulting formulation was subjected to stability tests:

Example 6: Physicochemical Data of Pendimethalin+Metribuzin ZC

| Sr no | Properties | | Ambient | 14 days AHS 54° C. |
|---|---|---|---|---|
| 1 | Appearance | | Orange yellow capsule suspension | Flowable, Orange yellow capsule suspension |
| 2 | Pendimethalin ai content | | 389.31 | 388.8 |
| 3 | Metribuzin ai content | | 68.07 | 67.72 |
| 4 | Suspensibility % w/w | | 104.3 | 102.31 |
| 5 | Spontaneity of dispersion % w/w | | 105.3 | 103.26 |
| 6 | Wet sieve retention % w/w | | 0.02 | 0.03 |
| 7 | pH as such | | 7.15 | 7.29 |
| 8 | Pourability rinse residue % | | 0.05 | 0.05 |
| 9 | Particle size | D-50 | 7.38 | 7.58 |
| | | D-4.3 | 10.0 | 10.2 |
| | | D-90 | 14.9 | 16.50 |

Conclusion:

1) The formulation showed good stability of physicochemical properties, suspensibility, spontaneity of dispersion, pH range, wet sieve retention, particle size in AHS at 54° C.

2) The formulation showed improved AI stability in AHS.

Example 6: Low Temperature Stability of Pendimethalin+Metribuzin ZC

| Sr no | Properties test | | Before Freeze/Thaw | After Freeze/Thaw test |
|---|---|---|---|---|
| 1 | Appearance | | Orange yellow capsule suspension | Flowable, Orange yellow capsule suspension |
| 2 | Pendimethalin ai content g/L | | 389.31 | 389.19 |
| 3 | Metribuzin ai content g/L | | 68.07 | 67.95 |
| 4 | Suspensibility % w/w | | 104.3 | 103.6 |
| 5 | Wet sieve retention % w/w | | 0.02 | 0.03 |
| 6 | pH as such | | 7.15 | 7.21 |
| 7 | Particle size | D-50 | 7.38 | 7.41 |
| | | D-4.3 | 10.0 | 10.1 |
| | | D-90 | 14.9 | 15.1 |

Conclusions:

Free pendimethalin in the formulation was very low and both capsule stability and suspension stability in low temperature was excellent.

Example 7: Real Time Stability Data for Pendimethalin+Metribuzin ZC

| Sr no | Properties | | Zero day | 6 month | 12 month |
|---|---|---|---|---|---|
| 1 | Appearance | | Orange yellow capsule suspension | Flowable, Orange yellow capsule suspension | Flowable, Orange yellow capsule suspension |
| 2 | Pendimethalin ai content g/L | | 389.31 | 388.72 | 388.14 |
| 3 | Metribuzin ai content g/L | | 68.07 | 66.78 | 66.43 |
| 4 | Suspensibility % w/w | | 104.3 | 99.68 | 99 |
| 5 | Spontaneity of dispersion % w/w | | 105.3 | 100.12 | 101.0 |
| 6 | Wet sieve retention % w/w | | 0.02 | 0.02 | 0.02 |
| 7 | pH 1% aqueous dispersion | | 7.15 | 6.91 | 6.80 |
| 9 | Particle size. | D-50 | 7.38 | 6.05 | 5.03 |
|   |   | D-4,3 | 10.0 | 8.8 | 8.64 |
|   |   | D-90 | 14.9 | 15.8 | 17.9 |

Conclusion:

1) Formulation demonstrated stability of physicochemical properties like suspensibility, spontaneity of dispersion, pH range, wet sieve retention, particle size etc. in AHS at 54° C. and in real time storage over a period of 12 months.

2) Both Pendimethalin and Metribuzin showed good stability in AHS, and real time storage.

Example 8: Pendimethalin+Triazine Herbicide Combination

Pendimethalin capsule suspension was prepared as described in example 1. Atrazine suspension concentrate was prepared according to the following formulation:

| sr no | Component of Formulation | % |
|---|---|---|
| 1 | Pendimethalin 18.1% @ 40% purity CS | 45.25 |
| 2 | Atrazin 18.1% @ 50% purity slurry | 36.2 |
| 3 | 2% Rhodopol-23 gel | 2.50 |
| 4 | R-100M | 2.00 |
| 5 | Proxel gxl | 0.10 |
| 6 | Water | 13.95 |
|   | Total | 100.00 |

The above composition was prepared by the following process:

An aqueous solution was prepared using water, sodium lignosulfonate, and antifoam agent. Atrazine was added to the mixture and homogenized. The homogenized solution was ground to particle size of $D_{90}$ 8-10 microns in a bead mill to form slurry.

The microencapsulated pendimethalin was added to the suspension concentrate of atrazine to form the final ZC formulation. The resulting formulation was subjected to stability tests:

Example 9: Physicochemical Data of Pendimethalin+Atrazin ZC

| Sr no | Properties | | Ambient | 14 days AHS |
|---|---|---|---|---|
| 1 | Appearance | | Orange yellow capsule suspension | Flowable, Orange yellow capsule suspension |
| 2 | Pendimethalin ai content g/L | | 206.99 | 205.98 |
| 3 | Atrazine ai content g/L | | 206.69 | 205.50 |
| 4 | Suspensibility % w/w | | 103.91 | 102.69 |
| 5 | Spontaneity of dispersion % w/w | | 100.83 | 100.11 |
| 6 | Wet sieve retention % w/w | | 0.01 | 0.03 |
| 7 | pH as such | | 7.31 | 7.48 |
| 8 | Pourability rinse residue % | | 0.03 | 0.08 |
| 9 | Particle size | D-50 | 3.75 | 3.42 |
|   |   | D-4,3 | 6.67 | 6.07 |
|   |   | D-90 | 14.4 | 13.6 |

Conclusion of ZC Formulation of Pendimethalin with Atrazine:

1) Formulation demonstrated good stability of physicochemical properties like suspensibility, spontaneity of dispersion, pH range, wet sieve retention, particle size etc. in AHS at 54° C. and in real time storage.
2) Formulation demonstrated excellent stability in AHS.

Example 10: Low Temperature Stability

| Sr no | Properties | | Before freeze/Thaw test | After freeze/Thaw test |
|---|---|---|---|---|
| 1 | Appearance | | Orange yellow capsule suspension | Flowable, Orange yellow capsule suspension |
| 2 | Pendimethalin ai content g/L | | 206.99 | 206.27 |
| 3 | Atrazin ai content g/L | | 206.69 | 206.50 |
| 4 | Suspensibility % w/w | | 103.91 | 101.73 |
| 5 | Wet sieve retention % w/w | | 0.01 | 0.05 |
| 6 | pH as such | | 7.31 | 7.42 |
| 7 | Particle size. | D-50 | 3.75 | 3.41 |
|   |   | D-4,3 | 6.67 | 6.62 |
|   |   | D-90 | 14.4 | 14.3 |

Conclusion:

Formulation was found to be stable in freeze/thaw cycle and maintained its physicochemical properties as ambient sample.

Example 11: Pendimethalin+Alkanamide Herbicide ZC Formulation

Pendimethalin capsule suspension was prepared as described in example 1. D-Napropamide suspension concentrate was prepared according to the following formulation:

| sr no | Component of Formulation | % |
|---|---|---|
| 1 | D-Napropamide 52% @ 98 | 53.06 |
| 2 | Borresperse NA | 7.00 |
| 3 | Defoamer (SAG-1572) | 0.50 |
| 4 | Water(QS) | 39.44 |
|  | Total | 100.00 |

The above composition was prepared by the following process:

An aqueous solution was created using water, sodium lignosulfonate, and antifoam agent. D-Napropamide was added to the mixture and homogenized. The homogenized solution was ground to particle size of $D_{90}$ 8-10 microns in a bead mill to form slurry.

The microencapsulated pendimethalin was added to the suspension concentrate of D-napropamide to form the final ZC formulation. The resulting formulation was subjected to stability tests:

Example 12: Physicochemical Data of Pendimethalin+D-Napropamide ZC

| Sr no | Properties | | Ambient | 14 days AHS |
|---|---|---|---|---|
| 1 | Appearance | | Orange yellow capsule suspension | Flowable, Orange yellow capsule suspension |
| 2 | Pendimethalin ai content g/L | | 241.01 | 240.8 |
| 3 | D-Napropamide ai content g/L | | 221.2 | 221.0 |
| 4 | Suspensibility % w/w | | 98.3 | 99.0 |
| 5 | Spontaneity of dispersion % w/w | | 99.89 | 100.2 |
| 6 | Wet sieve retention % w/w | | 0.04 | 0.05 |
| 7 | 1% aqueous suspension | | 7.69 | 7.58 |
| 8 | Pourability rinse residue % | | 0.18 | 0.21 |
| 9 | Particle size | D-50 | 4.35 | 4.16 |
|  |  | D-4,3 | 8.54 | 8.32 |
|  |  | D-90 | 14.5 | 14.7 |

Conclusion of ZC Formulation of Pendimethalin with D-Napropamide:

1) Formulation demonstrated excellent stability of physicochemical properties like suspensibility, spontaneity of dispersion, pH range, wet sieve retention, particle size etc. in AHS at 54° C. and in real time storage.
2) Both Pendimethalin and D-Napropamide demonstrated excellent stability in AHS.

Example 13: Low Temperature Stability of Pendimethalin+D-Napropamide

| Sr no | Properties | | Before freeze/Thaw test | After freeze/Thaw test |
|---|---|---|---|---|
| 1 | Appearance | | Orange yellow capsule suspension | Flowable, Orange yellow capsule suspension |
| 2 | Pendimethalin ai content g/L | | 241.01 | 240.92 |
| 3 | D-Napropamide ai content g/L | | 221.2 | 221.45 |
| 4 | Suspensibility % w/w | | 98.3 | 98.96 |
| 5 | Wet sieve retention % w/w | | 0.04 | 0.06 |
| 6 | pH as such | | 7.35 | 7.48 |
| 7 | Particle size | D-50 | 4.35 | 4.26 |
|  |  | D-4,3 | 8.54 | 8.45 |
|  |  | D-90 | 14.5 | 14.61 |

Conclusions:

Formulation was found to stable in freeze/thaw cycle and maintained its physicochemical properties as ambient sample.

Example 14: Pendimethalin+Imidazolinone Herbicide ZC Formulations

Pendimethalin capsule suspension was prepared as described in example 1. Imidazolinone herbicides imazapic and Imazathapyr were formulated into suspension concentrates according to the following formulation:

| Sr. no | Component of Formulation | Imazapic acid | Imazathapyr acid |
|---|---|---|---|
| 1 | Imidazolinone 96% purity tech | 46.4 | 52.08 |
| 2 | Borropsperse NA | 7.00 | 7.00 |
| 3 | Defoamer (SAG-1572) | 0.50 | 0.50 |
| 4 | Water(QS) | 46.1 | 40.42 |
|  | Total | 100.00 | 100.00 |

The above composition was prepared by the following process:

An aqueous solution was prepared using water, capsule suspension of pendimethalin, sodium lignosulfonate, and antifoam agent. The imidazolinone was added to the mixture and homogenized to obtain final ZC formulation.

Example 15: Pendimethalin+Imazapic Acid ZC Formulation

Pendimethalin capsule suspension was prepared as the described in example 1. Imazapic was formulated into suspension concentrate according to the following formulation

| sr no | Component of Formulation | % |
|---|---|---|
| 1 | Pendimethalin 31.3 @ 40.7% Purity CS | 76.90 |
| 2 | Imazapic acid 8.5@ 45% purity slurry | 18.88 |
| 3 | Reax-100M | 2.00 |
| 4 | 2% Rhodopol-23 gel | 1.00 |
| 5 | Proxel GXL | 0.10 |
| 6 | Water (QS) | 1.12 |
|  | total | 100.00 |

The above composition was prepared by following process:

An aqueous solution was prepared using water, capsule suspension of pendimethalin, sodium lignosulfonate, xanthan gum, biocide. The mixture was homogenized. Imazapic was added to the mixture and homogenized to obtain final ZC formulation. The formulation was found to be stable at ambient temperature.

Example 16: Pendimethalin+Organophosphorus Herbicide ZC Formulation

Pendimethalin capsule suspension was prepared as the described in example 1. Glyphosate suspension concentrate was prepared according to the following formulation:

| Sr. no | Component of Formulation | % w/w |
|---|---|---|
| 1 | Glyphosate acid 45 @ 96 | 46.4 |
| 2 | Borresperse NA | 7.00 |
| 3 | Defoamer (SAG-1572) | 0.50 |
| 4 | Water(QS) | 46.1 |
| | Total | 100.00 |

The above composition was prepared by following the process as follows:

An aqueous solution was prepared using water, sodium lignosulfonate, and antifoam agent. Glyphosate acid was added to the mixture and homogenized. The homogenized solution was ground to particle size of $D_{90}$ 8-10 microns in a bead mill to form slurry.

The microencapsulated pendimethalin was added to the suspension concentrate of glyphosate acid to form the final ZC formulation.

Example 17: Pendimethalin+Glyphosate ZC Formulation

Pendimethalin capsule suspension was prepared as the described in example 1. Glyphosate suspension concentrate was prepared according to the following formulation:

| sr no | Component of Formulation | % |
|---|---|---|
| 1 | Pendimethalin 27 @ 40.7% Purity CS | 66.34 |
| 2 | Glyphosate acid 11.75@ 45% purity slurry | 26.11 |
| 3 | Reax-100M | 2.00 |
| 4 | 2% Rhodopol-23 gel | 2.00 |
| 5 | Proxel GXL | 0.10 |
| 6 | Water (QS) | 3.45 |
| | total | 100.00 |

The above composition was prepared by the following process:

An aqueous solution was prepared using water, capsule suspension of pendimethalin, sodium lignosulfonate, and xanthan gum. Glyphosate was added to the mixture and homogenized to obtain final ZC formulation. The formulation was found to be stable at ambient temperature.

Comparative Examples

Pendimethalin compositions were prepared using other formulation types to compare efficacy, stability and compatibility with respect to ZC formulation:

Example 18A: Pendimethalin+Pyrazosulfuron Ethyl WP Formulations

Pendimethalin WP Composition

| Sr. No. | Ingredients | % w/w |
|---|---|---|
| 1 | Pendimethalin 45.5% @ 96% purity | 47.40 |
| 2 | M-fill A-100 | 26.94 |
| 3 | Metasperse 550S | 8 |
| 4 | Supragil WP | 4.5 |
| 5 | defoamer DC1920 | 1 |
| 5 | Ammonium sulphate | 10 |
| | Total | 97.85 |

Pyrazosulfuron Ethyl WP Composition

| Sr. No. | Ingredients | % w/w |
|---|---|---|
| 1 | PSE 1.1% @ % purity tech | 1.16 |
| 2 | Supragil WP | 0.50 |
| 3 | M-fill A-100 | 0.5 |
| | Total | 2.15 |

Process:—
Step-1: Pendimethalin Premix
a) Pendimethalin was melted and absorbed into precipitated silica by slow addition at low rpm of a mixer bowl and kept overnight.
b) Mixed Metasperse 550s (Modified styrene acrylic polymer), Supragil WP (dialkyl naphthalene sulphonate sodium salt), ammonium sulphate and Defoamer DC1920 powder in above Pendimethalin+silica mixture of step a) and mixed for homogeneity.
c) Ground the premix on Air jet mill to get lump free material.
Step-2:—Pyrazosulfuron-Ethyl Premix
a) Pyrazosulfuron-ethyl technical, Supragil WP (dialkyl naphthalene sulphonate sodium salt) and M-fill A-100 (precipitated silica) were mixed and ground in an air jet mill to obtain a particle size $D_{98}$ 30-36 micron.
Step-3:—mixing
The Pendimethalin premix of Step 1 and Pyrazosulfuron-premix of step 2 were mixed to obtain final WP formulation.

The resulting formulation was then subjected to stability tests:

Physicochemical Data of Pendimethalin+Pyrazosulfuron Ethyl WP:

| Sr no | Properties | Ambient | 6 week AHS at 45° C. | 7 month Real time data |
|---|---|---|---|---|
| 1 | Appearance | Yellow Free flowing powder | Yellow-orange powder slight soft lump | Yellow-orange powder |
| 2 | Pendimethalin ai content % w/w | 45.87 | 45.75 | 45.67 |
| 3 | Pyrazosulfuron ethyl ai content % w/w | 1.05 | 1.002 (4.5% degradation) | 0.92 (12% degradation) |
| 4 | Suspensibility % w/w gravimetric | 84.39 | 68 | 58 |
| 5 | Wetting time in sec | 40 | 20 | 30 |
| 6 | Wet sieve retention % w/w | 0.07 | 0.30 | 1.62 |

-continued

| Sr no | Properties | Ambient | 6 week AHS at 45° C. | 7 month Real time data |
|---|---|---|---|---|
| 7 | pH 1% aqueous suspension | 6.89 | 6.71 | 6.80 |

Conclusion:
1. Formulation showed a drop in suspensibility in AHS and real time storage.
2. Pyrazosulfuron-ethyl degradation was found to be 12% in only 7 month of real time storage, which is very high as compared to the stable formulations of Example 1.
3. Formulation showed rise in wet sieve retention in AHS, and intense rise in wet sieve ie 1.68% in only 7 month of real time storage.

Example 18B: Pendimethalin+Metribuzin WP Formulations 8.2.1 Pendimethalin WP Composition

| Sr. No. | Ingredients | % w/w |
|---|---|---|
| 1 | Pendimethalin 38.7% @ 97% purity | 39.90 |
| 2 | M-fill A-100 | 22 |
| 3 | Metasperse 550S | 7 |
| 4 | Supragil WP | 4.5 |
| 5 | Defoamer DC1920 | 1 |
| 5 | Ammonium sulphate | 15.05 |
| | Total | 89.45 |

8.2.2 Metribuzin WP Composition

| Sr. No. | Ingredients | % w/w |
|---|---|---|
| 1 | Metribuzin 6.7% @ 95% purity tech | 7.05 |
| 2 | Supragil WP | 0.50 |
| 3 | M-fill A-100 | 2.00 |
| 4 | Metasperse 550S | 1.00 |
| | Total | 10.55 |

Process:—
Step-1: Pendimethalin Premix
a) M-fill A-100 (Precipitated silica), Metasperse 550s (Modified styrene acrylic polymer), and Supragil WP (Modified styrene acrylic polymer) were added in mixer bowl and absorbed the molten Pendimethalin tech by slow addition at slow rpm.
b) Ammonium sulphate and Defoamer DC1920 powder were then added and mixed for homogeneity. The material was kept overnight.
Step-2:—Metribuzin Premix
c) Metribuzin tech, Metasperse 550 S (Modified styrene acrylic polymer), Supragil WP (Modified styrene acrylic polymer) and M-fill A-100 (Precipitated silica) were pre mixed and ground on the air jet mill to get particle size $D_{98}$ 30-36 micron.
Step-3:—Mixing
The Pendimethalin premix of Step 1 and metribuzin premix of step 2 were mixed to obtain final WP formulation.

The resulting formulation was then subjected to stability tests:
Physicochemical Data of Pendimethalin+Metribuzin WP

| Sr. no | Properties | Ambient | 6 week AHS at 45° C. |
|---|---|---|---|
| 1 | Appearance | Yellow Free flowing powder | Yellow-orange powder slight soft lump |
| 2 | Pendimethalin ai content % w/w | 38.57 | 38.53 |
| 3 | Metribuzin ai content % w/w | 6.75 | 6.72 |
| 4 | Suspensibility % w/w | 88.48 | 40.29 |
| 5 | Wetting time in sec | 17 | 30 |
| 6 | Wet sieve retention % w/w | 0.12 | 0.48 |
| 7 | pH 1% aqueous suspension | 7.27 | 7.01 |

Conclusion of WP Formulation of Pendimethalin with Metribuzin:
1. Formulation showed decreased suspensibility in AHS and real time storage in 6 weeks.
2. Formulation showed rise in wet sieve retention in AHS.
3. There was a soft lump in AHS, which is undesirable.
As used herein, the term ZC shall be used to denote mixed formulations of capsule suspensions and suspension concentrates, each of which may comprise a single herbicide or a combination of herbicides such as herein described. ZC is therefore an aqueous suspension of microcapsules and solid particles, each of which may comprise one or more herbicidal active ingredients according to the present invention. The capsule suspension component typically comprises encapsulated pendimethalin, optionally along with another herbicide. The suspension concentrate component typically includes another herbicide or combination of herbicides.

The invention claimed is:
1. A ZC formulation comprising:
(a) a capsule suspension formulation of pendimethalin; and
(b) a suspension concentrate comprising particles of a first herbicide;
wherein the capsule suspension formulation comprises microcapsules comprising pendimethalin encapsulated within a polymeric wall formed in-situ by an interfacial polymerization reaction occurring between an organic phase dispersed in an aqueous phase, said aqueous phase comprising at least one alkali or alkaline earth metal salt of an organic acid, said organic acid is selected from the group consisting of acetic acid, propionic acid, citric acid, fumaric acid, tartaric acid, oxalic acid, succinic acid, valeric acid, malonic acid, glutaric acid, adipic acid and phthalic acid, with the proviso that the aqueous phase does not comprise an inorganic salt prior to formation of the polymeric wall; and
wherein the capsule suspension formulation comprises about 1% to about 20% polymeric wall by weight; and about 2% to about 55% the at least one alkali or alkaline earth metal salt of an organic acid by weight.
2. The ZC formulation according to claim 1, wherein the capsule suspension has reduced staining property as compared to an encapsulated pendimethalin formulation that comprises an inorganic salt, prior to formation of the polymeric wall, within the microcapsule.
3. The ZC formulation according to claim 1, wherein the first herbicide is known to be incompatible with pendimethalin.

4. The ZC formulation according to claim 1, wherein the first herbicide is selected from the group consisting of:
(a) a sulfonylurea herbicide selected from the group consisting of amidosulfuron, azimsulfuron, bensulfuron or bensulfuron methyl, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, methiopyrisulfuron, monosulfuron, nicosulfuron, orthosulfamuron, oxasulfuron, primisulfuron, propyrisulfuron, pyrazosulfuron or pyrazosulfuron-ethyl, rimsulfuron, sulfometuron, sulfosulfuron, trifloxysulfuron, chlorsulfuron, cinosulfuron, ethametsulfuron, iodosulfuron, iofensulfuron, metsulfuron or metsulfuron methyl, prosulfuron, thifensulfuron, triasulfuron, tribenuron, triflusulfuron, and tritosulfuron;
(b) a triazinone herbicide selected from the group consisting of ametridione, amibuzin, ethiozin, hexazinone, isomethiozin, metamitron, metribuzin, and trifludimoxazin;
(c) a imidazolinone herbicide selected from the group consisting of imazamethabenz, imazamox, imazapic, imazapyr, imazaquin, and imazethapyr;
(d) a triazine herbicide selected from the group consisting of dipropetryn, trihydroxytriazine, atrazine, chlorazine, cyanazine, cyprazine, eglinazine, ipazine, mesoprazine, procyazine, proglinazine, propazine, sebuthylazine, simazine, terbuthylazine trietazine, indaziflam, triaziflam, atraton, methometon, prometon, secbumeton, simeton, terbumeton, ametryn, aziprotryne, cyanatryn, desmetryn, dimethametryn, methoprotryne, prometryn, simetryn, and terbutryn;
(e) an anilide herbicide selected from the group consisting of chloranocryl, cisanilide, clomeprop, cypromid, diflufenican, erlujixiancaoan, etobenzanid, fenasulam, flufenacet, flufenican, ipfencarbazone, mefenacet, mefluidide, metamifop, monalide, naproanilide, pentanochlor, picolinafen, propanil, sulfentrazone, and triafamone;
(f) a sulfonamide herbicide selected from the group consisting of asulam, carbasulam, fenasulam, oryzalin, penoxsulam, and pyroxsulam;
(g) an organophosphorus herbicide selected from the group consisting of amiprofos-methyl, amiprophos, anilofos, bensulide, bilanafos, butamifos, clacyfos, fosamine, glufosinate and all its salts and esters, glufosinate-P, glyphosate and all its salts and esters, huangcaoling, piperophos, and shuangjiaancaolin
(h) an amide herbicide selected from the group consisting of allidochlor, amicarbazone, beflubutamid, benzadox, benzipram, bromobutide, cafenstrole, 2-chloro-N-N-diethylacetamide (CDEA), cyprazole, dimethenamid, dimethenamid-P, diphenamid, epronaz, etnipromid, fentrazamide, flucarbazone, flupoxam, fomesafen, halosafen, huangcaoling, isocarbamid, isoxaben, napropamide, napropamide-M, pethoxamid, propyzamide, quinonamid, tebutam, and tiafenacil;
(i) a quinolinecarboxylic acid herbicide selected from the group consisting of quinclorac, and quinmerac;
(j) a benzoylcyclohexanedione herbicide selected from the group consisting of fenquinotrione, ketospiradox, mesotrione, sulcotrione, tefuryltrione, and tembotrione;
(k) a benzofuranyl alkylsulfonate herbicide selected from the group consisting of benfuresate, and ethofumesate;
(l) a chloroacetanilide herbicide selected from the group consisting of acetochlor, alachlor, butachlor, butenachlor, delachlor, diethatyl, dimethachlor, ethachlor, ethaprochlor, metazachlor, metolachlor, S-metolachlor, pretilachlor, propachlor, propisochlor, prynachlor, terbuchlor, thenylchlor, and xylachlor;
(m) a nitrophenyl ether herbicide selected from the group consisting of acifluorfen, aclonifen, bifenox, chlomethoxyfen, chlornitrofen, etnipromid, fluorodifen, fluoroglycofen, fluoronitrofen, fomesafen, fucaomi, furyloxyfen, halosafen, lactofen, nitrofen, nitrofluorfen, and oxyfluorfen; and
(m) a dinitroanaline herbicide selected from the group consisting of benfluralin, butralin, chlornidine, dinitramine, dipropalin, ethalfluralin, fluchloralin, isopropalin, methalpropalin, nitralin, oryzalin, prodiamine, profluralin, and trifluralin.

5. The ZC formulation according to claim 1, wherein the first herbicide is selected from the group consisting of sulfonylurea herbicide, triazinone herbicide, imidazolinone herbicide, triazine herbicide, anilide herbicide, sulphonamide herbicide, organophosphorus herbicide, amide herbicide, quinolinecarboxylic acid herbicide, benzoylcyclohexanedione herbicide, benzofuranyl alkyl sulfonate herbicide, nitrophenyl ether herbicide, and alkanamide herbicide.

6. The ZC formulation according to claim 1, wherein the first herbicide is selected from the group consisting of pyrazosulfuron-ethyl, metribuzin, imazapic acid, atrazine, napropamide, napropamide-M, flufenacet, oryzalin, glufosinate, glyphosate, and agrochemically acceptable derivatives thereof.

7. The ZC formulation according to claim 1, wherein the suspension concentrate further comprises a second herbicide.

8. A kit comprising:
(a) the ZC formulation according to claim 1; and
(b) instructions for administering the ZC composition.

9. A method for controlling undesirable plant species at a locus, said method comprising applying to the desired locus a herbicidally effective amount of a ZC formulation according to claim 1.

10. A ZC formulation comprising:
(a) a capsule suspension formulation of pendimethalin; and
(b) a suspension concentrate comprising particles of one or more herbicides;
wherein the capsule suspension formulation comprises microcapsules comprising pendimethalin encapsulated within a polymeric wall formed in-situ by an interfacial polymerization reaction occurring between an organic phase dispersed in an aqueous phase, said aqueous phase comprising at least one alkali or alkaline earth metal salt of an organic acid, said organic acid is selected from the group consisting of acetic acid, propionic acid, citric acid, fumaric acid, tartaric acid, oxalic acid, succinic acid, valeric acid, malonic acid, glutaric acid, adipic acid and phthalic acid, with the proviso that the aqueous phase does not comprise an inorganic salt prior to formation of the polymeric wall;
wherein the capsule suspension formulation comprises about 1% to about 20% polymeric wall by weight; and about 2% to about 55% the at least one alkali or alkaline earth metal salt of an organic acid by weight; and
wherein the one or more herbicides is selected from the group consisting of sulfonylurea herbicide, triazinone herbicide, imidazolinone herbicide, triazine herbicide, anilide herbicide, sulphonamide herbicide, organophosphorus herbicide, amide herbicide, quinolinecarboxylic acid herbicide, benzoylcyclohexanedione herbicide, benzofuranyl alkyl sulfonate herbicide, nitrophenyl ether herbicide, and alkanamide herbicide.

11. A kit comprising:
(a) the ZC formulation according to claim 10; and
(b) instructions for administering the ZC composition.

12. A method for controlling undesirable plant species at a locus, said method comprising applying to the desired locus a herbicidally effective amount of a ZC formulation according to claim 10.

13. A ZC formulation comprising:
(a) a capsule suspension formulation of pendimethalin; and
(b) a suspension concentrate comprising particles of one or more herbicides;
wherein the capsule suspension formulation comprises microcapsules comprising pendimethalin encapsulated within a polymeric wall formed in-situ by an interfacial polymerization reaction occurring between an organic phase dispersed in an aqueous phase, said aqueous phase comprising at least one alkali or alkaline earth metal salt of an organic acid, said organic acid is selected from the group consisting of acetic acid, propionic acid, citric acid, fumaric acid, tartaric acid, oxalic acid, succinic acid, valeric acid, malonic acid, glutaric acid, adipic acid and phthalic acid, with the proviso that the aqueous phase does not comprise an inorganic salt prior to formation of the polymeric wall;
wherein the capsule suspension formulation comprises about 1% to about 20% polymeric wall by weight; and about 2% to about 55% the at least one alkali or alkaline earth metal salt of an organic acid by weight; and
wherein the one or more herbicides is selected from the group consisting of pyrazosulfuron-ethyl, metribuzin, imazapic acid, atrazine, napropamide, napropamide-M, flufenacet, oryzalin, glufosinate, glyphosate, and agrochemically acceptable derivatives thereof.

14. A kit comprising:
(a) the ZC formulation according to claim 13; and
(b) instructions for administering the ZC composition.

15. A method for controlling undesirable plant species at a locus, said method comprising applying to the desired locus a herbicidally effective amount of a ZC formulation according to claim 13.

* * * * *